(12) United States Patent
Watanabe et al.

(10) Patent No.: US 10,980,904 B2
(45) Date of Patent: Apr. 20, 2021

(54) AERATION METHOD OF ISOLATOR SYSTEM

(71) Applicant: SHIBUYA CORPORATION, Kanazawa (JP)

(72) Inventors: Soma Watanabe, Kanazawa (JP); Yusuke Hirosawa, Kanazawa (JP); Katsuki Hashimoto, Kanazawa (JP)

(73) Assignee: SHIBUYA CORPORATION, Kanazawa (JP)

( * ) Notice: Subject to any disclaimer, the term of this patent is extended or adjusted under 35 U.S.C. 154(b) by 182 days.

(21) Appl. No.: 15/954,137

(22) Filed: Apr. 16, 2018

(65) Prior Publication Data

US 2018/0311389 A1 Nov. 1, 2018

(30) Foreign Application Priority Data

May 1, 2017 (JP) .............................. JP2017-090965

(51) Int. Cl.
| | | |
|---|---|---|
| *A61L 2/20* | (2006.01) | |
| *C12M 3/00* | (2006.01) | |
| *C12M 1/00* | (2006.01) | |
| *C12M 1/12* | (2006.01) | |
| *A61G 11/00* | (2006.01) | |

(52) U.S. Cl.
CPC ................. *A61L 2/20* (2013.01); *A61L 2/208* (2013.01); *C12M 23/44* (2013.01); *C12M 37/00* (2013.01); *C12M 41/14* (2013.01); *A61G 11/005* (2013.01); *A61L 2202/14* (2013.01); *A61L 2202/15* (2013.01)

(58) Field of Classification Search
CPC ........ A61L 2/20; A61L 2/208; A61L 2202/15; A61L 2202/14; C12M 37/00; C12M 41/14; C12M 23/44; A61G 11/005
See application file for complete search history.

(56) References Cited

U.S. PATENT DOCUMENTS

| | | | | |
|---|---|---|---|---|
| 9,086,225 | B2 * | 7/2015 | Tanimoto | ................ F24F 3/161 |
| 9,222,066 | B2 * | 12/2015 | Tanimoto | ............... C12M 41/14 |

(Continued)

FOREIGN PATENT DOCUMENTS

| | | | | |
|---|---|---|---|---|
| JP | 2006068122 | * | 3/2006 | ............... A61L 2/20 |
| JP | 4924570 B2 | | 3/2010 | |
| WO | WO-2015111431 A1 | * | 7/2015 | ............ C12M 41/40 |

*Primary Examiner* — Regina M Yoo
(74) *Attorney, Agent, or Firm* — Flynn Thiel, P.C.

(57) ABSTRACT

In an aeration method for an isolator system, an incubator is connected to an isolator through a chamber. After closing a door at each sidewall of the chamber, a decontaminating gas is supplied to the chamber through gas supply passages to decontaminate the inside thereof. Next, air is supplied into the chamber through the gas supply passages and an initial aeration is carried out by discharging the decontamination gas through a gas discharge passage. Then, after a door between the isolator and the chamber is opened, and blowers are stopped, gas at a positive pressure in the isolator is introduced into the chamber. The decontaminating gas in the chamber is rapidly discharged to an outside through the gas supply passages and the gas discharge passage, and aeration in the chamber is completed.

The time required for aeration of the chamber can be drastically reduced as compared with conventional aeration processes.

3 Claims, 5 Drawing Sheets

(56) References Cited

U.S. PATENT DOCUMENTS

| | | | | |
|---|---|---|---|---|
| 9,789,480 | B2* | 10/2017 | Funazuka | B01L 1/04 |
| 9,878,062 | B2* | 1/2018 | Shomura | A61L 2/20 |
| 2012/0202485 | A1* | 8/2012 | Mirbaha | H04W 76/45 |
| | | | | 455/426.1 |
| 2012/0273047 | A1* | 11/2012 | Yokoi | C12M 23/44 |
| | | | | 137/1 |
| 2012/0275965 | A1* | 11/2012 | Yokoi | C12M 37/00 |
| | | | | 422/187 |
| 2012/0275967 | A1* | 11/2012 | Yokoi | A61L 2/208 |
| | | | | 422/291 |
| 2013/0336844 | A1* | 12/2013 | Yokoi | A61L 2/208 |
| | | | | 422/111 |
| 2015/0017063 | A1* | 1/2015 | Yokoi | C12M 37/00 |
| | | | | 422/28 |
| 2015/0139855 | A1* | 5/2015 | Tanimoto | C12M 29/20 |
| | | | | 422/30 |
| 2016/0184814 | A1* | 6/2016 | Funazuka | B25J 21/02 |
| | | | | 422/565 |
| 2016/0339130 | A1* | 11/2016 | Shomura | C12M 41/40 |

* cited by examiner

AERATION METHOD OF ISOLATOR SYSTEM

BACKGROUND OF THE INVENTION

Field of the Invention

The present invention relates to an aeration method of an isolator system and more particularly to an aeration method of an isolator system which can aerate an inside of a chamber in a short time after the inside of the chamber is decontaminated by a decontaminating gas when an incubator is connected to the isolator through the chamber, for example.

Description of the Related Art

Conventionally, an isolator system including an isolator as an aseptic work room, a pass box as a chamber connected to the isolator and carrying in and removing an article to and from the isolator, a filter provided on a gas inflow portion and a gas outflow portion of the isolator, decontaminating gas supply means for supplying the decontaminating gas into the isolator and the pass box, and aeration means for carrying out aeration after decontamination of the isolator and the pass box (see Japanese Patent No. 4924570, for example).

In a regenerative medical field, the incubator is replaced with respect to the isolator through the chamber by connecting the incubator to the isolator through the chamber, during work in the isolator and by decontaminating only the chamber in that state.

In a device in the aforementioned Japanese Patent No. 4924570, for example, when the pass box, as the chamber connected to the isolator is to be decontaminated, the inside of the pass box is decontaminated first, and then the inside of the pass box is aerated through a HEPA filter provided on a suction side. Thus, a component of the decontaminating gas remaining in the HEPA filter enters into the pass box, and aeration inside the pass box takes too much time, which is a problem.

SUMMARY OF THE INVENTION

In view of the aforementioned circumstances, the present invention is, in an aeration method of an isolator system including an isolator as an aseptic work room whose inside is maintained at a positive pressure, an opening/closing door opening/closing an opening portion of the isolator, a chamber connected to the opening portion of the isolator from an outside of the isolator and allowing carrying in/out of an article to/from the isolator, decontaminating gas supply means for supplying a decontaminating gas into the chamber, a gas supply passage connecting the decontaminating gas supply means and the chamber, and a gas discharge passage for discharging the gas inside the chamber to an outside and comprised such that after the inside of the chamber is decontaminated by supplying the decontaminating gas into the chamber, the gas inside the chamber is discharged to the outside and the inside of the chamber is aerated, the inside of the chamber is decontaminated by supplying the decontaminating gas into the chamber through the gas supply passage in a state where the opening/closing door is closed; and after that, the opening/closing door is opened in a state where the inside of the isolator is maintained at a positive pressure, the gas at the positive pressure in the isolator is introduced into the chamber through the opening portion, the gas in the chamber is discharged to the outside through at least either one of the gas supply passage and the gas discharge passage, and aeration inside the chamber is carried out.

According to such constitution, the gas containing the decontaminating gas in the chamber is discharged to the outside rapidly by the gas at the positive pressure from the isolator during the aeration. Moreover, the decontaminating gas remaining in the HEPA filter does not flow into the chamber. Therefore, time required for the aeration of the chamber can be drastically reduced as compared with before.

DETAILED DESCRIPTION OF THE PREFERRED EMBODIMENT

The present invention will be described below by the illustrated embodiment, and in FIG. 1, an isolator system 1 includes a box-shaped isolator 2 as an aseptic work room, a box-shaped incubator 3 for culturing cells therein, a cylindrical chamber 4 connecting the incubator 3 to the isolator 2 when necessary, decontaminating gas supply means 5 for supplying a decontaminating gas G into the isolator 2 and the chamber 4 and decontaminating insides thereof, first aeration means 6 for carrying out aeration after the decontamination inside the isolator 2, second aeration means 7 for carrying out the aeration after the decontamination inside the chamber 4, and a control device 8 for controlling an operation of driving source of each constituent element and the like.

An opening portion 2B is formed on a side wall 2A on a front side of the isolator 2, and an opening/closing door 11A for opening and closing the opening portion 2B from an inner side is provided. Moreover, an opening portion 2D is also formed on a side wall 2C on a rear side, and an opening/closing door 11B for opening and closing the opening portion 2D from an inner side is provided. When the opening portions 2B and 2D are closed by the opening/closing doors 11A and 11B, the inside of the isolator 2 is sealed.

A pass box, not shown, is connected outside of the opening portion 2B. By opening or closing the opening/closing door 11A, an article such as a culture vessel or the like can be carried into and out of the isolator 2 through the pass box and the opening portion 2B. Moreover, in a state where the incubator 3 is connected to the opening portion 2D through the chamber 4, by opening or closing the opening/closing door 11B, the article in the isolator 2 can be carried into the incubator 3 through the chamber 4 and the opening portion 2D or the article in the incubator 3 can be carried into the isolator 2.

Moreover, a work glove, not shown, is provided on the side wall of the isolator 2 so that a worker can insert the hand into the work glove and then carries out required work in the isolator 2.

Regarding the incubator 3, an opening portion 3B is formed on a side wall 3A on a front surface, and an opening/closing door 12 for opening or closing this opening portion 3B from an inner side is provided. After a vessel accommodating cells is accommodated in the incubator 3, the opening portion 3B is closed by the opening/closing door 12, and culture of the cells is carried out by storing it for a required period in that state. Since a caster, not shown, is provided on a bottom part of the incubator 3, the worker can push and move the incubator 3 to a required position.

The chamber 4 is formed cylindrically, an opening portion 4A on a front side is connected to the opening portion 2D of the isolator 2 while air tightness is held, and an opening portion 4B on a rear side can be connected to the opening portion 3B of the incubator 3 while air tightness is held.

When the incubator 3 is to be connected to the isolator 2, the worker moves the incubator 3 closer to the isolator 2, and then connects the opening portion 4B to the opening portion 3B of the incubator 3. As a result, the incubator 3 can be connected to the opening portion 2D of the isolator 2 through the chamber 4.

By opening the opening/closing door 11B in such a connected state, the inside of the chamber 4 and the inside of the isolator 2 are made to communicate with each other, and by further opening the opening/closing door 12, the inside of the incubator 3 and the inside of the chamber 4 are made to communicate with each other. By opening the opening/closing doors 11B and 12 after decontamination and aeration inside the chamber 4 (which will be described later in detail), the article in the isolator 2 can be carried into the incubator 3 through the opening portions 2D and 3B and the chamber 4. The opening and closing of each of the opening/closing doors 11A, 11B, and 12 is performed by the worker manually by using the work glove. It may be so constituted that robots are arranged in the isolator 2 or in the incubator 3 to automatically open and close each of the opening/closing doors 11A, 11B, and 12.

The decontaminating gas supply means 5 includes a tank 13 reserving a hydrogen peroxide solution, a pipe 15 connecting this tank 13 and a gas generating portion 14 to each other, a pump P1 arranged in the middle of the pipe 15 and feeding the hydrogen peroxide solution to the gas generating portion 14, and a gas supply passage 16 for connecting the gas generating portion 14 and the isolator 2 and supplying the decontaminating gas G (hydrogen peroxide gas) to the isolator 2.

An operation of the pump P1 is controlled by the control device 8, and when the control device 8 operates the pump P1, the hydrogen peroxide solution in the tank 13 is supplied to the gas generating portion 14 through the pipe 15, and the decontaminating gas G is generated therein.

One end of the gas supply passage 16 communicates with the inside of the isolator 2 through a HEPA filter F1 arranged on a top surface 2E of the isolator 2. The HEPA filter F1 includes a function of purifying a gas flowing therethrough. A normally-closed electromagnetic opening/closing valve V1 is provided in the middle of the gas supply passage 16, and an operation of this electromagnetic opening/closing valve V1 is controlled by the control device 8.

The gas generating portion 14 is connected to a blower B1 by an air feeding pipe 17, and a catalyst S1 decomposing and detoxifying the decontaminating gas G is provided in the middle of the air feeding pipe 17. Operation of the blower B1 is controlled by the control device 8.

In a state where the decontaminating gas G is generated in the gas generating portion 14, when the electromagnetic opening/closing valve V1 is opened by the control device 8, and the blower B1 is operated, air is fed to the gas generating portion 14 by the blower B1 through the air feeding pipe 17, and the air containing the decontaminating gas G is further supplied into the isolator 2 through the gas supply passage 16 and the HEPA filter F1. At this time, both opening/closing doors 11A and 11B are closed. In this way, by means of the supply of the decontaminating gas G into the isolator 2, the inside of the isolator 2 is decontaminated.

A fan 21 for diffusing the decontaminating gas G is provided in the isolator 2, and when the fan 21 is operated by the control device 8, the decontaminating gas G is diffused over the whole area in the isolator 2. Moreover, a pressure gauge 22 for measuring a pressure inside the isolator 2 is provided, and the pressure in the isolator 2 measured by the pressure gauge 22 is transmitted to the control device 8.

On an upper side of the isolator 2, an air supply passage 23 for supplying the air is arranged, and an end portion on an inner side of this air supply passage 23 is made to communicate with the inside of the isolator 2 through the HEPA filter F1. In the middle of the air supply passage 23, a blower B2 for feeding the air toward the isolator 2 is arranged, and a catalyst S2 is provided in the middle of the air passage 23 outside of the blower B2. The catalyst S2 is arranged as a safety device for decomposing and detoxifying the decontaminating gas G when the decontaminating gas G flows backward in the air supply passage 23. Moreover, an electromagnetic opening/closing valve V2 is provided at a position on a downstream side from the blower B2 in the air supply passage 23.

On the other hand, on a lower side of the isolator 2, an air discharge passage 24 is arranged, and an end portion on an inner side of this air discharge passage 24 is made to communicate with the inside of the isolator 2 through a HEPA filter F2 arranged on a bottom surface 2F of the isolator 2. In the middle of the air discharge passage 24, a blower B3 for air discharge is provided, and a catalyst S3 for detoxifying the decontaminating gas G is provided between the blower B3 and the HEPA filter F2. Moreover, a normally-closed electromagnetic opening/closing valve V3 is provided at a position on an upstream side from the catalyst S3 in the air discharge passage 24. Operation of the electromagnetic opening/closing valves V2, V3 and the blowers B2, B3 are controlled by the control device 8.

The air supply passage 23 on the air feeding side and the electromagnetic opening/closing valve V2 provided in the air supply passage 23, the blower B2, the catalyst S2, the air discharge passage 24 on the air discharge side, the electromagnetic opening/closing valve V3 provided in the air discharge passage 24, the blower B3, and the catalyst S3 constitute the first aeration means 6.

In the state where both opening/closing doors 11A and 11B are closed, the inside of the isolator 2 is decontaminated by the decontaminating gas G with the procedure described above. After the inside of the isolator is decontaminated, aeration in the isolator 2 is carried out by the first aeration means 6. That is, when the control device 8 operates the electromagnetic opening/closing valves V2, V3 and the blowers B2, B3, the air is supplied into the isolator 2 through the air supply passage 23, and the gas containing the decontaminating gas G in the isolator 2 is discharged to the outside through the air discharge passage 24.

As a result, the gas containing the decontaminating gas G in the isolator 2 is discharged and is replaced by the air, and aeration is carried out. Then, when the control device 8 controls the operations of the blowers B2, B3 so that both blowers B2, B3 are continuously operating, the inside of the isolator 2 is maintained at a predetermined positive pressure higher than the atmospheric pressure.

Then, this embodiment is characterized in that, on the premise of the constitution described above, when the incubator 3 is connected to the isolator 2 by the chamber 4, after the inside of the chamber 4 is decontaminated, the inside of the chamber 4 can be aerated in a short time.

That is, the chamber 4 is connected to the middle of the gas supply passage 16 by the gas supply passage 26, and the chamber 4 can discharge the gas inside it by the gas discharge passage 27 to the outside.

Connectors 28A and 28B capable of connection and separation are provided in the middle of the gas supply passage 26, and they are connected or separated when necessary. Moreover, a HEPA filter F3 for purifying the gas is provided in the gas supply passage 26 closer to the chamber 4 than the connectors 28A and 28B. That is, the HEPA filter F3 is provided in the middle of the gas supply passage 26 which is outside of the chamber 4.

In the state where the connectors 28A and 28B are connected, the gas supply passage 16 located between the electromagnetic opening/closing valve V1 and the gas generating portion 14 is made to communicate with the inside of the chamber 4 through the gas supply passage 26. That is, the gas generating portion 14 communicates with the inside of the chamber 4. In this connection state, when the electromagnetic opening/closing valve V1 is closed and the blower B1 is operated by the control device 8 in a state where the decontaminating gas G is generated by the gas generating portion 14, the decontaminating gas G is supplied into the chamber 4 through the gas supply passages 16 and 26. At that time, since both opening/closing doors 11B and 12 are closed, the inside of the chamber 4 is decontaminated. The connection and separation of the connectors 28A and 28B are performed by the worker manually. The connection of the connectors 28A and 28B may be automatically made by a cylinder or the like.

On the other hand, connectors 29A and 29B capable of connection and separation are provided in the middle of the gas discharge passage 27, and they are connected or separated when necessary.

In the gas discharge passage 27 on the downstream side from the connectors 29A and 29B, a catalyst S4 for sequentially detoxifying the decontaminating gas and a blower B4 for discharging the gas to the outside are provided. Moreover, in a gas discharge passage 27 between the connectors 29A and 29B and the chamber 4, a HEPA filter F4 for purifying the gas is provided. The HEPA filter F4 is provided in the middle of the gas discharge passage 27 outside of the chamber 4. Operation of the blower B4 is controlled by the control device 8, while the connection and separation of the connectors 29A and 29B is performed by the worker manually.

In the state where the connectors 29A and 29B are connected, the inside of the chamber 4 can communicate with the outside air through the gas discharge passage 27. When the blower B4 is operated by the control device 8 in this connection state, the gas in the chamber 4 is discharged to the outside through the gas discharge passage 27. At that time, the decontaminating gas contained in the gas is detoxified by the catalyst S4.

In this embodiment, the blowers B1, B4, the catalysts S1, S4, the HEPA filters F3, F4, the gas supply passages 16, 26, and the gas discharge passage 27 constitute the aforementioned second aeration means 7.

As described above, in this embodiment, the gas supply passage 26 and the gas discharge passage 27 are connected to the chamber 4, and the decontamination of the inside of the chamber 4 and the aeration after that are carried out by using them and the aforementioned opening/closing doors 11B and 12.

In the aforementioned constitution, in the isolator system 1 of this embodiment, first, the decontamination in the isolator 2 and the aeration after that are carried out, and then required work is carried out in the isolator 2. When necessary, the incubator 3 is connected to the isolator 2 by the chamber 4 during the work in the isolator 2.

That is, first, when the opening/closing doors 11A and 11B are closed after the article is carried into the isolator 2, the pump P1 is operated and the decontaminating gas G is generated in the gas generating portion 14. In that state, the electromagnetic opening/closing valve V1 is opened and the blower B1 is operated by the control device 8. At this time, the connectors 28A and 28B are not connected.

Then, air is fed by the blower B1 to the gas generating portion 14 through the air feeding pipe 17, and the air containing the decontaminating gas G is supplied into the isolator 2 through the gas supply passage 16 and the HEPA filter F1. At this time, since the fan 21 in the isolator 2 is also operated, the decontaminating gas G is diffused over the whole area in the isolator 2. In this way, by means of the supply of the decontaminating gas G into the isolator 2 for a predetermined time, the inside of the isolator 2 is decontaminated.

After that, the operations of the blower B1, the pump P1, the fan 21, and the electromagnetic opening/closing valve V1 are stopped, and the electromagnetic opening/closing valve V1 is closed.

After that, the electromagnetic opening/closing valves V2 and V3 are opened, and the blowers B2 and B3 are operated synchronously, and thus, the air is supplied into the isolator 2 through the air supply passage 23 and the HEPA filter F1, and the gas containing the decontaminating gas G in the isolator 2 is discharged to the outside of the isolator 2 through the air discharge passage 24. In this way, the inside of the isolator 2 is aerated for a predetermined time, and when the inside of the isolator 2 reaches a predetermined positive pressure, the operations of the blowers B2 and B3 are continued while the work is being performed. In this way, the aeration in the isolator 2 is completed, and then, in a state where the inside of the isolator 2 is maintained at the positive pressure, the worker performs required work in the isolator 2 by using the work glove (not shown).

Figure 2:
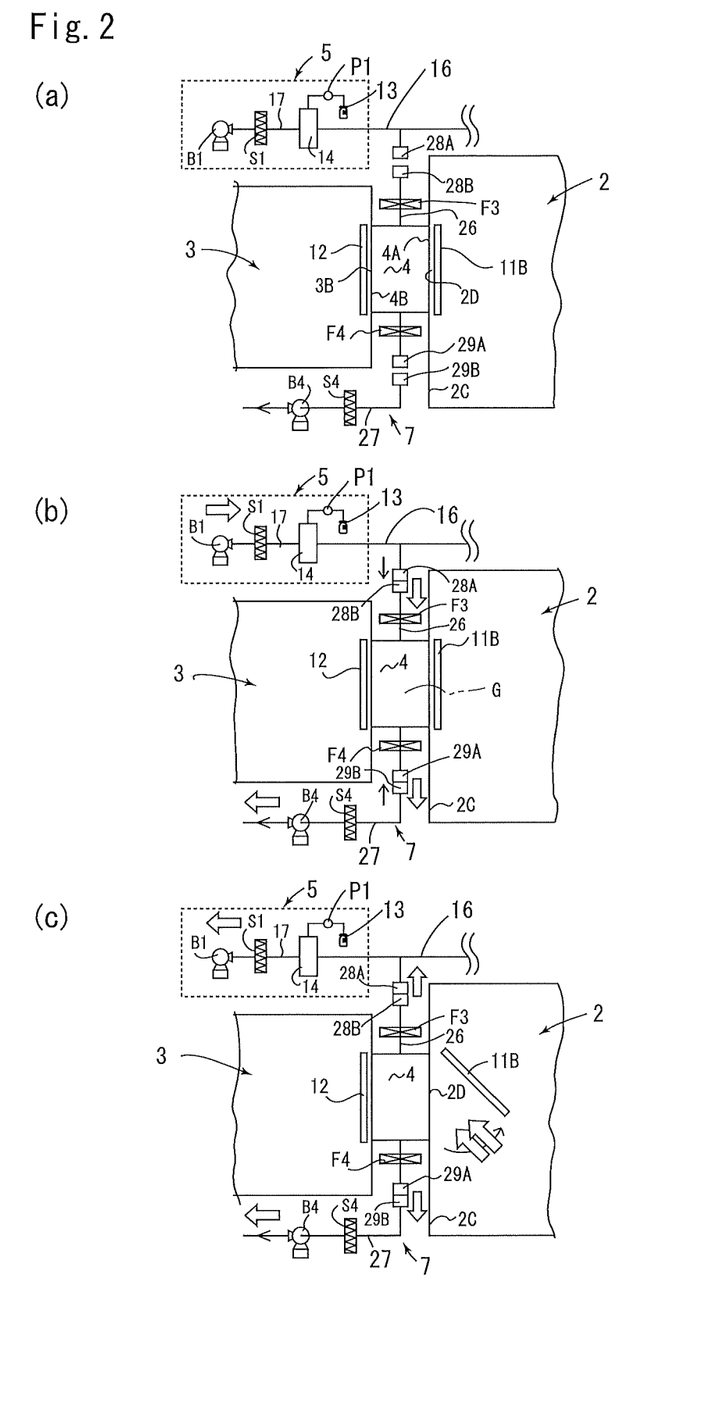
FIG. 2 is a work process diagram when an essential part in FIG. 1 is decontaminated, and then aeration is carried out.

During the work in the isolator 2, when a need to connect the incubator 3 to the isolator 2 arises, the incubator 3 is connected to the isolator 2 by the chamber 4 (see FIG. 2(a)). That is, the opening portion 4B of the chamber 4 is connected to the opening portion 3B of the incubator 3. In this state, the opening portion 2D of the isolator 2 is closed by the opening/closing door 11B, and the opening portion 3B of the incubator 3 is closed by the opening/closing door 12. Thus, the chamber 4 does not communicate with the isolator 2 and the incubator 3.

After that, the connectors 28A and 28B which have been separated are connected by the worker, and the connectors 29A and 29B are also connected by the worker. After that, a leakage check of the chamber 4 is performed by a leakage checker, not shown.

After that, the decontamination in the chamber 4 and the aeration after that are carried out. That is, first, the pump P1 and the blowers B1 and B4 are operated, and thus, the decontaminating gas G is supplied into the chamber 4 by the blower B1 through the decontaminating gas supply passage 16 and the gas supply passage 26 connected to that. When this state is maintained for a predetermined time, the inside of the chamber 4 is decontaminated by the decontaminating gas G (see FIG. 2(b)).

When the predetermined time has elapsed since start of the decontamination and the decontamination in the chamber 4 is finished, the pump P1 is stopped while the blower B1 is still operated. After that, the air is supplied into the chamber 4 from the blower B1 through the gas supply passages 16 and 26 and, at the same time, the gas containing the decontaminating gas G in the chamber 4 is discharged to the outside through the gas discharge passage 27. As a result, initial aeration of the inside of the chamber 4 is carried out (see FIG. 2(b)).

After that, after the opening/closing door 11B on the isolator 2 side is opened by the worker, the operations of the blowers B1 and B4 are stopped. Here, since the isolator 2 is maintained at the predetermined positive pressure as described above, the gas at the positive pressure in the isolator 2 is rapidly introduced into the chamber 4, and then it is discharged to the outside through the gas discharge passage 27 and the HEPA filter F4 arranged therein, the catalyst S4, and the blower B4. Moreover, it is also discharged to the outside through the HEPA filter F3, the catalyst S1, the gas supply passages 26 and 16, and the air feeding pipe 17 at the same time (see FIG. 2(c)). As a result, the gas containing the decontaminating gas G in the chamber 4 is rapidly discharged to the outside. At that time, since the catalysts S1 and S4 are arranged in the air feeding pipe 17 and the gas discharge passage 27 respectively, a harmful component in the gas is detoxified and discharged to the outside. As a result, the aeration in the chamber 4 is completed.

As described above, in this embodiment, after the initial aeration is carried out for the chamber 4 for the predetermined time after the decontamination, the opening/closing door 11B is opened, the gas at the positive pressure is introduced to the chamber 4, and the aeration is carried out.

After that, by opening the opening/closing door 12 of the incubator 3, the incubator 3 and the isolator 2 communicate with each other through the chamber 4. In that state, the article in the isolator 2 is carried into the incubator 3 through the opening portions 2D and 3B and the chamber 4, and after that, the opening/closing doors 11B and 12 are closed.

As described above, in this embodiment, the HEPA filter F3 is arranged in the middle of the gas supply passage 26 outside of the chamber 4, and the HEPA filter F4 is arranged in the middle of the gas discharge passage 27 outside of the chamber 4.

Then, the inside of the chamber 4 is aerated by introducing the gas at the positive pressure in the isolator 2 into the chamber 4 after the decontamination. Thus, the component of the decontaminating gas G remaining in the HEPA filters F3 and F4 does not enter into the chamber 4 during the aeration, and the gas containing the decontaminating gas G in the chamber 4 is rapidly discharged to the outside by the gas at the positive pressure from the isolator 2. Therefore, the time required for the aeration of the chamber 4 can be drastically reduced as compared with before.

Figure 3:
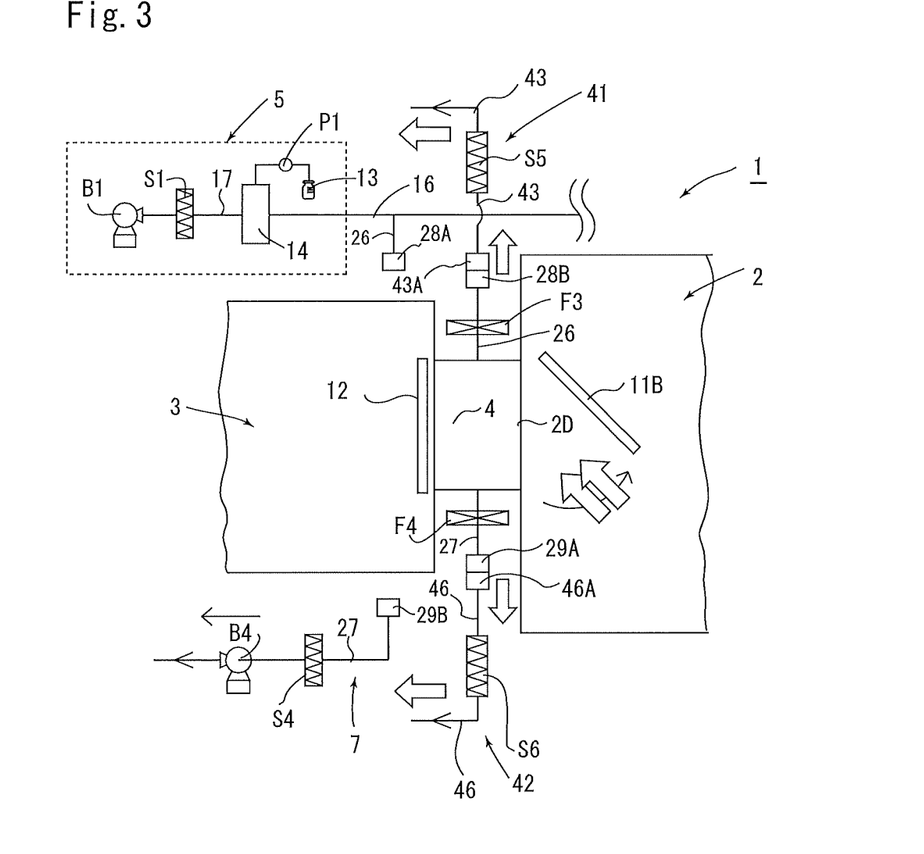
FIG. 3 is a constitution diagram illustrating another embodiment of the present invention.

FIG. 3 illustrates another embodiment relating to the aeration of the chamber 4, and a first catalyst unit 41 and a second catalyst unit 42 are added to the constitution in the aforementioned first embodiment.

The first catalyst unit 41 is constituted by a connection pipe 43, a connector 43A provided on one end thereof, and a catalyst S5 provided in the middle of the connection pipe 43. The second catalyst unit 42 is constituted by a connection pipe 46, a connector 46A provided on one end thereof, and a catalyst S6 provided in the middle of the connection pipe 46. The other constitutions are the same as those of the aforementioned first embodiment, and the same numbers are given to each of the members corresponding to them.

Then, after the inside of the chamber 4 is decontaminated by the decontaminating gas, the connector 43A of the connection pipe 43 is connected to the connector 28B of the gas supply passage 26, and the connector 46A of the connection pipe 46 is connected to the connector 29A of the gas discharge passage 26. That is, the connection pipe 43 of the first catalyst unit 41 is connected to the gas supply passage 26, and the connection pipe 46 of the second catalyst unit 42 is connected to the gas discharge passage 27. In this state, by opening the opening/closing door 11B of the isolator 2, the gas at the positive pressure in the isolator 2 is introduced into the chamber 4, and thus, the gas in the chamber 4 is rapidly discharged to the outside through the connection pipes 43 and 46, and the aeration of the chamber 4 can be carried out.

With such a constitution, actions and effects similar to those of the aforementioned first embodiment can be obtained. Moreover, in this embodiment, such an effect can be also obtained that, during the aeration in the chamber 4, the decontaminating gas can be supplied to other required spots by the decontaminating gas supply means 5.

Figure 4:
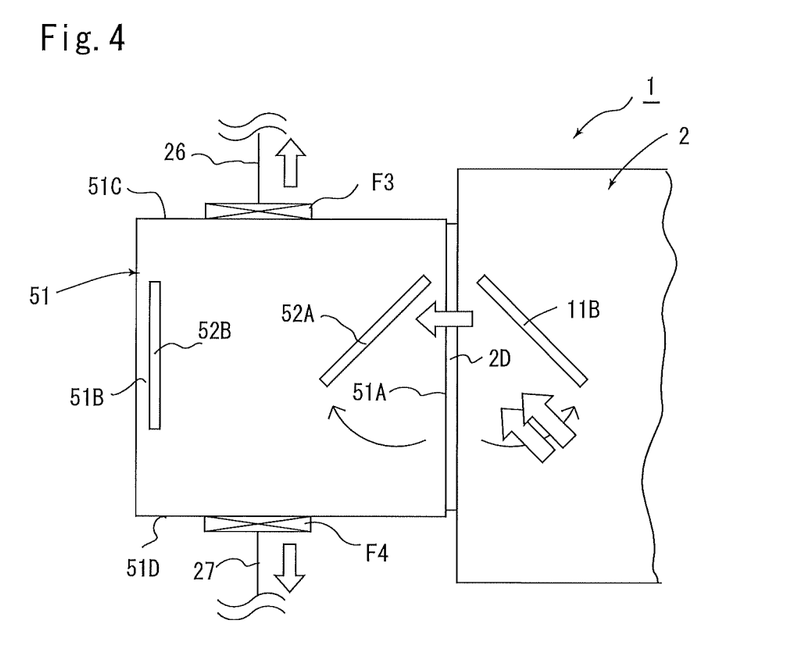
FIG. 4 is a constitution diagram illustrating another embodiment of the present invention.

FIG. 4 illustrates another embodiment of the present invention. In this embodiment, the present invention applies a pass box 51 as a chamber connected to the isolator 2 instead of the chamber 4 for connecting the isolator 2 and the incubator 3. In the box-shaped pass box 51, a pair of opening portions 51A and 51B and opening/closing doors 52A and 52B for opening or closing them from inside are provided. The pass box 51 is connected to the opening portion 2D of the isolator 2.

The HEPA filter F3 is provided on an outer surface 51C of one of the side walls of the pass box 51, and the gas supply passage 26 is connected through that. Moreover, the HEPA filter F4 is provided on an outer surface 51D of the other side wall of the pass box 51, and the gas discharge passage 27 is connected through that. The other constitutions are similar to those in the first embodiment illustrated in FIG. 1.

In this embodiment, one end of the gas supply passage 26 is connected to this pass box 51 through the HEPA filter F3 on the outer side, and one end of the gas discharge passage 27 is connected to the pass box 51 through the HEPA filter F4 on its outer side.

In this embodiment, in a state where the pass box 51 is connected to the opening portion 2D of the isolator 2, and the opening/closing doors 52A and 52B are closed, the inside of pass box 51 is decontaminated with the same procedure as the aforementioned other embodiments. After that, by opening the opening/closing door 52A and the opening/closing door 11B of the isolator 2, the gas at the positive pressure in the isolator 2 is introduced into the pass box 51, and thus, the inside of the pass box 51 can be rapidly aerated.

Figure 5:
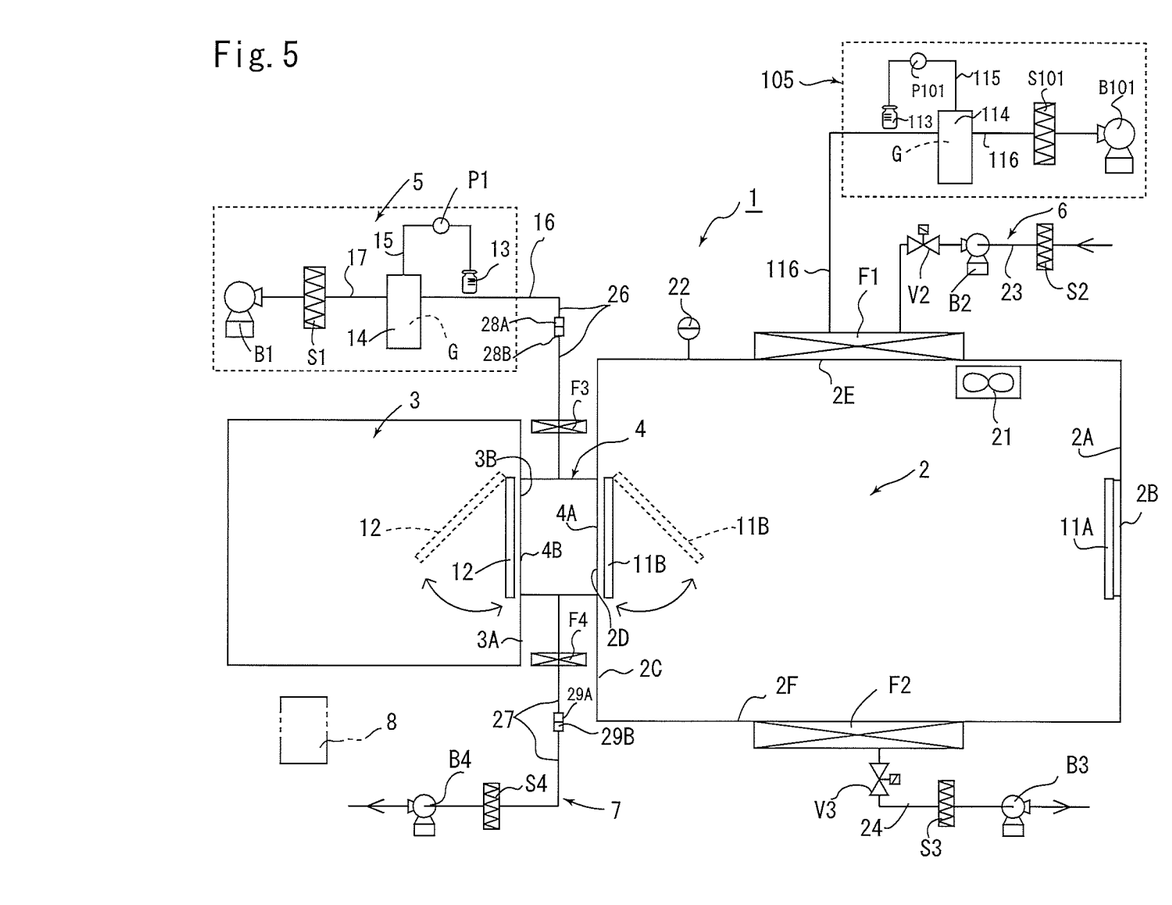
FIG. 5 is a constitution diagram illustrating another embodiment of the present invention.

FIG. 5 illustrates another embodiment of the present invention. This embodiment is characterized in that, a second decontaminating gas supply means 105 exclusive for the isolator 2 is added in addition to the decontaminating gas supply device 5.

Figure 1:
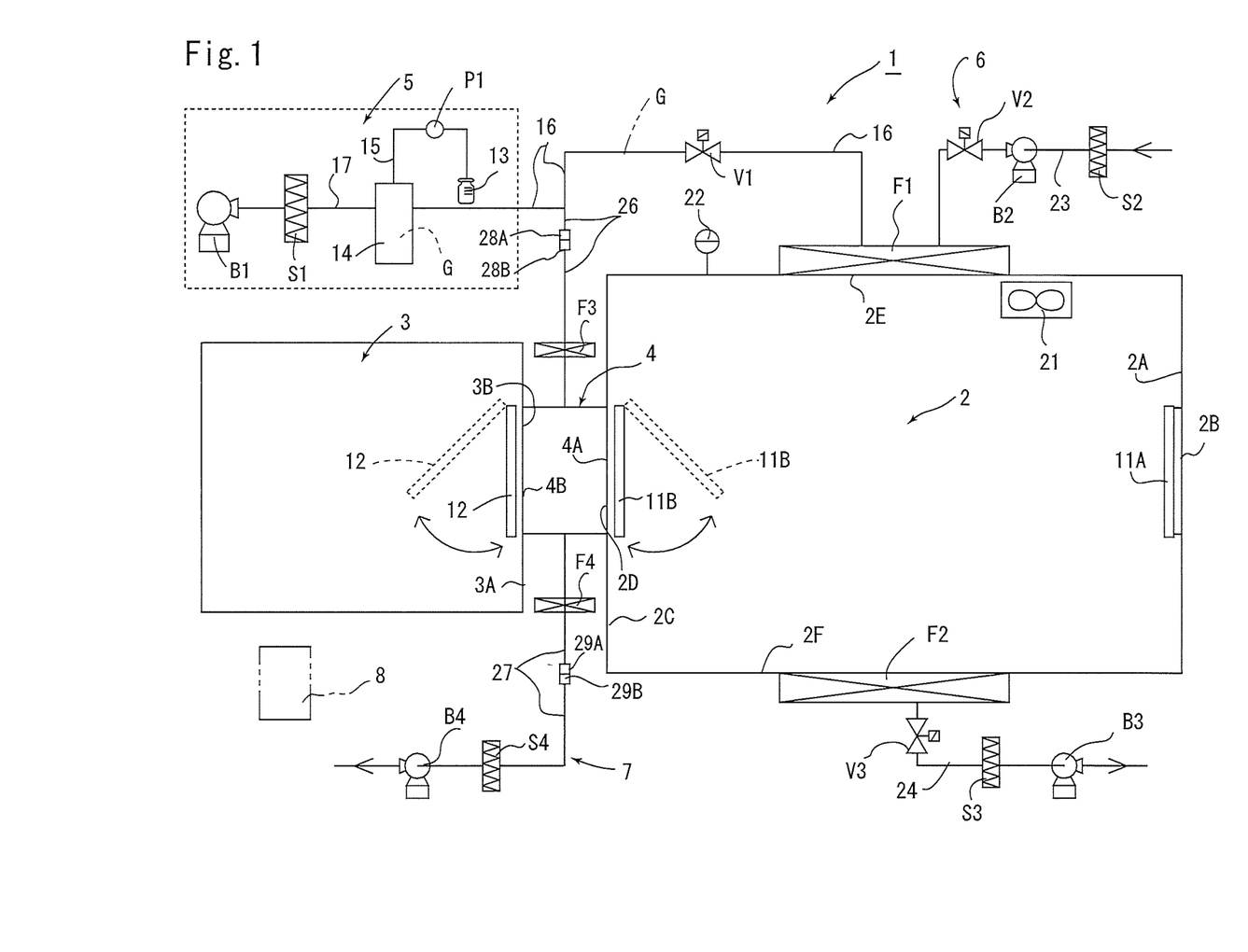
FIG. 1 is a constitution diagram illustrating an embodiment of the present invention in its entirety.

That is, in the embodiment illustrated in FIG. 1, the decontaminating gas G is supplied from the decontaminating gas supply means 5 to the chamber 4 through the gas supply passages 16 and 26 connected by the connectors 28A and 28B. The decontaminating gas G is supplied only to the chamber 4 from the decontaminating gas supply means 5.

On the other hand, in the embodiment illustrated in FIG. 5, the second decontaminating gas supply means 105 constituted similarly to the aforementioned decontaminating gas supply means 5 is provided, and the decontaminating gas G can be supplied into the isolator 2 from the decontaminating gas supply means 105 through the gas supply passage 116 connected to the HEPA filter F1. Constituent elements of the decontaminating gas supply means 105 are the same as those of the decontaminating gas supply means 5, where reference numbers to which 100 is added to the corresponding constituent elements are given, respectively. The other constitutions are the same as those in the embodiment in FIG. 1, and the same reference numbers are given to the corresponding constituent elements, respectively.

In the embodiment in FIG. 5, the decontaminating gas G is supplied from the decontaminating gas supply means 105 in the decontamination of the isolator 2, while the decontaminating gas G is supplied from the decontaminating gas supply means 5 in the decontamination of the chamber 4. The other operations are similar to those in the aforementioned first embodiment. In the embodiment illustrated in FIG. 5, the actions and effects are also similar to those of the embodiment in the aforementioned FIG. 1 can be obtained.

The aforementioned embodiment assumes a case where the incubator 3 is connected to the isolator 2 through the chamber 4, but it can also be applied to a case where a material module or the like is connected to the isolator 2 through the chamber 4.

REFERENCE SIGNS LIST

1 isolator system,
2 isolator,
2D opening portion,
4 chamber,
5 decontaminating gas supply means,
11B opening/closing door,
16,26 gas supply passages,
27 gas discharge passage,
F3 HEPA filter (first filter),
F4 HEPA filter (second filter),
G decontaminating gas

What is claimed is:

1. An aeration method of an isolator system comprising an isolator as an aseptic work room whose inside is maintained at a positive pressure, a door for opening and closing an opening portion of the isolator, a chamber connected to the opening portion of the isolator from outside of the isolator and allowing insertion and removal of an article in the isolator, a decontaminating gas supplier for supplying a decontaminating gas into the chamber, a gas supply passage connecting the decontaminating gas supplier and the chamber, and a gas discharge passage for discharging the decontaminating gas inside the chamber to outside of the chamber, the decontaminating gas supplier including a tank containing a hydrogen peroxide solution and a pump which feeds the hydrogen peroxide solution to a gas generating portion, wherein:

the inside of the chamber is decontaminated by supplying the decontaminating gas into the chamber through the gas supply passage in a state where the door is closed; and after that, the door is opened in a state where the inside of the isolator is maintained at a positive pressure, a gas at the positive pressure in the isolator is introduced into the chamber through the opening portion, the decontaminating gas in the chamber is discharged to the outside of the chamber through the gas supply passage and the gas discharge passage, and aeration inside the chamber is carried out.

2. The aeration method of an isolator system according to claim 1, including a first filter provided in a portion of the gas supply passage outside of the chamber for purifying the decontaminating gas passing through the gas supply passage and a second filter provided in a portion of the gas discharge passage outside of the chamber for purifying the decontaminating gas flowing through the gas discharge passage.

3. The aeration method of an isolator system according to claim 1, wherein the decontaminating gas in the chamber is discharged to the outside of the chamber simultaneously through the gas supply passage and the gas discharge passage.

* * * * *